Figure 1:
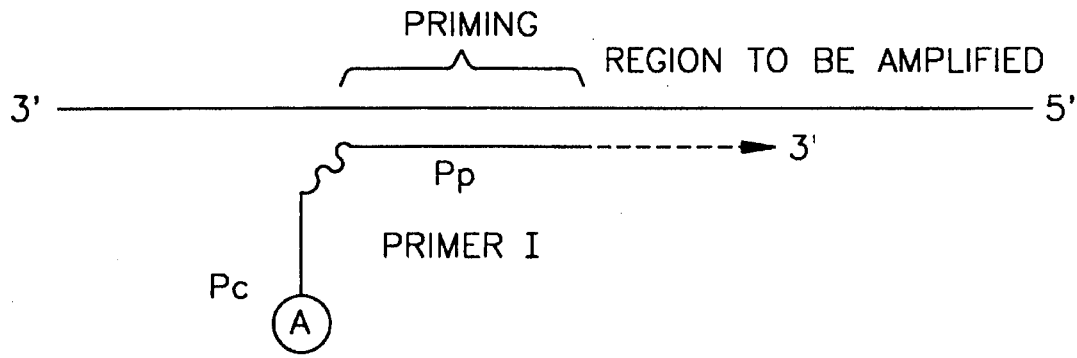
Figure 1:
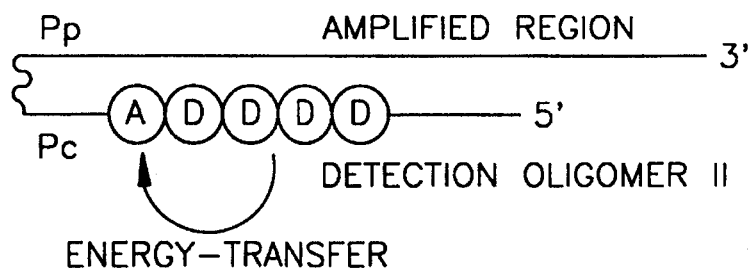
Figure 1:
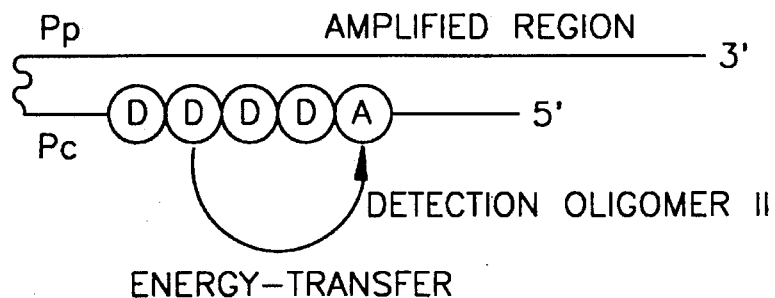

United States Patent [19]

Bannwarth et al.

[11] Patent Number: 5,573,906
[45] Date of Patent: Nov. 12, 1996

[54] DETECTION OF NUCLEIC ACIDS USING A HAIRPIN FORMING OLIGONUCLEOTIDE PRIMER AND AN ENERGY TRANSFER DETECTION SYSTEM

[75] Inventors: Wilhelm Bannwarth, Upper Saddle River, N.J.; Francis Muller, Basel, Switzerland

[73] Assignee: Hoffmann-La Roche Inc., Nutley, N.J.

[21] Appl. No.: 35,010

[22] Filed: Mar. 22, 1993

[30] Foreign Application Priority Data

Mar. 23, 1992 [EP] European Pat. Off. .............. 92104956

[51] Int. Cl.⁶ .............. C12Q 1/68; C12P 19/34; C07H 21/04
[52] U.S. Cl. .............. 435/6; 435/91.2; 536/24.33; 536/24.3; 935/77; 935/78
[58] Field of Search .............. 435/6, 91.2; 536/24.33, 536/24.3; 935/77, 78, 79

[56] References Cited

FOREIGN PATENT DOCUMENTS 2033692  1/1991  Canada .
201184   3/1986  European Pat. Off. .
427073  10/1990  European Pat. Off. .
439036   1/1991  European Pat. Off. .

OTHER PUBLICATIONS

Bannwarth et al. (1991) Helvetica Chimica Acta 74: 2000–2008.
Krupp et al. (1987) FEBS Lett. 212:271–275.
Uhlmann (1988) Gene 71:29–40.
Bej et al. (1991) Critical Reviews in Biochem & Mol. Biology 26(3/4):301–334.
Seela, et al., Nucleic Acids Research, 15:3113–3129 (1987) "Oligodeoxyribo-nucleotides containing 1,3–propanediol as nucleoside substitute".
Wu, et al., Genomics, 4:560–569 (1989) "The Ligation Amplification Reaction—Amplification of Specific DNA Seq. using Sequential Rounds of Template-Dep. Ligation".

*Primary Examiner*—W. Gary Jones
*Assistant Examiner*—Lisa Arthur
*Attorney, Agent, or Firm*—George M. Gould; William H. Epstein; Patricia S. Rocha-Tramaloni

[57] ABSTRACT

A process for the detection of a nucleic acid sequence in a homogeneous assay format using an energy transfer system is disclosed. This process utilizes a 5' labeled primer containing a selfcomplementary sequence in an amplification or extension process together with a subsequent detection step using a 3' labeled probe for the amplified or extended region. The labels will be close together in space after hybridizing the probe close to the short piece of double-stranded DNA resulting from backfolding of the selfcomplementary region of the primer which has been incorporated into the amplified or extended product. A new primer for use in this process is also disclosed.

21 Claims, 1 Drawing Sheet a) DENATURATION AND AMPLIFICATION ( HIGH TEMPERATURE)

b) DETECTION (LOW TEMPERATURE)

c)

Ⓓ :ENERGY DONOR
Ⓐ :ENERGY ACCEPTOR
⌇ :NONNUCLEOTIDYLIC LINKER L

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

ATAATCCACC TATCCCAGTA GGAGAAAT        28

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TATCCCAGTA GGAGAAAT        18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TATCCCAGTA GGAGAAAT        18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

TATCCCAGTA GGAGAAAT     18

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

TACTGGGATA     10

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

TATCCCAGTA GGAGAAAT     18

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TACTGGGATA     10

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

TTTGGTCCTT GTCTTATGTC CAGAATGC 28

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

CCAAACTCCG ATAATCCACC TATCCCAGTA GGAGAAAT 38

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

CGGAGTTTGG 10

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

TGGGATAGGT GGATTAT 17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

AGGTGGATAG GGTCATC 17

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

GCCACTTGTA TGCAACT     17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

TATTAGGTGG ATAGGGT     17

( 2 ) INFORMATION FOR SEQ ID NO:15:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

TATCCCAGTA GGAGAAATTT ATAAAAGATG GATAA     35

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

TACTGGGATA     10

( 2 ) INFORMATION FOR SEQ ID NO:17:

( i ) SEQUENCE CHARACTERISTICS:
        ( A ) LENGTH: 19 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

TTATCCATCT TTTATAAAT    19

(2) INFORMATION FOR SEQ ID NO:18:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

TATCCCAGTA GGAGAAATTT ATAAAGATG GATAA    35

(2) INFORMATION FOR SEQ ID NO:19:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

TTCTCCTACT GGGATA    16

(2) INFORMATION FOR SEQ ID NO:20:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

TTATCCATCT TTTATAAAT    19

DETECTION OF NUCLEIC ACIDS USING A HAIRPIN FORMING OLIGONUCLEOTIDE PRIMER AND AN ENERGY TRANSFER DETECTION SYSTEM

1. TECHNICAL FIELD

The present invention is directed to a process for detecting the presence or absence of a nucleic add sequence in a homogenous assay format using an energy transfer system. The described process uses a 5' labeled primer having a self complementary sequence in a primer extension/incorporation reaction or an amplification process followed by a subsequent detection step using a 3' labeled probe which is complementary to a portion of the extended product.

2. BACKGROUND

The polymerase chain reaction (PCR) is a very powerful method for the specific amplification of DNA or RNA stretches. The methodology is described in European Patent Applications, Pub. Nos. 201.184, 200.362 and 258.017. One application of this technology is in DNA probe technology to bring up DNA present in low copy numbers to a detectable level. Numerous diagnostic and scientific applications of this method have been described by H. A. Erlich (Ed.) in PCR Technology-Principles and Applications for DNA Amplification, Stockton Press, USA, 1989 and by M. A. Inis (Ed.) in PCR Protocols, Academic Press, San Diego, USA, 1990.

A desirable goal would be the direct detection of the amplified DNA without time-consuming separations or transfer steps by a so-called homogeneous assay format. At the same time the aim is also to replace radioactive labels still mainly utilized in DNA diagnostics by nonradioactive reporter systems thereby extending the applications of this technology. Such a homogeneous detection system applying intercalating chemiluminescent acridinium esters has been reported by Arnold et al. in Clinical Chemistry 35, 1588 (1989). Further variations of the homogeneous DNA detection assays are described in a review by B. S. Reckmann in Nachr. Chem. Tech. Lab. 37, 692–702 (1989).

The use of bathophenanthroline-Ru II complexes as non-radioactive label molecules which can be measured with high sensitivity by time-resolved fluorometry has been described by W. Bannwarth et al. in Helv. Chim. Acta 71, 2085–2099 (1988). These complexes can be part of an interactive pair of label molecules allowing energy transfers from suitable energy donor molecules to the Ru complex. Because the efficiency of the energy transfer is highly dependent on the distance between donor and acceptor molecules, such energy transfer systems are useful in studying molecule interactions.

A suitable class of donor molecules for use with Ru complexes is the lumazine chromophore group of molecules. The possible applicability of this donor/acceptor complex in the detection, inter alia, of DNA molecules in a homogeneous assay is described in European Patent Application, Publ. No. 439 036, and in Helvetica Chimica Acta 74, 1991–1999 (1991) and 74, 2000–2008 (1991) by W. Bannwarth and F. Müller. Using such a combination, energy transfers were detected within oligodeoxynucleotides labeled at the 5'-end with a Ru bathophenanthroline complex and possessing lumazine chromophores at different distances from the Ru complex within the oligonucleotide. It also was demonstrated that this pair of interactive labels is useful in detecting a target DNA sequence in a hybridization process wherein one probe sequence is equipped with the donor and the other with the acceptor.

An alternative approach using a terbium complex as an energy acceptor and salicylate as an energy donor in a homogeneous DNA detection system was described by A. Oser and G. Valet in Angewandte Chemie 102, 1197–1200 (1990).

Known processes for the detection of oligonucleotides in a homogeneous test format employing energy transfers for the subsequent detection typically use at least two labeled oligonucleotides that hybridize specifically, side by side, to the complementary DNA sequence thereby positioning the two labels next to each other.

3. DISCLOSURE OF THE INVENTION

The present invention is directed, inter alia, to a process for detecting the presence or absence of at least one specific nucleic acid sequence in a sample suspected of containing said sequence, which process comprises:

a) amplifying the nucleic acid sequence to be detected by means of a chain extension reaction utilizing a first oligonucleotide primer of general formula $$X\text{-}Pc\text{-}L\text{-}Pp \qquad (I)$$

wherein Pp is an oligonucleotide sequence substantially complementary to a part of one strand of the nucleic acid sequence to be detected, Pc is an oligonucleotide sequence substantially complementary to the sequence Pp, L is a non-nucleotidylic linker group selected so as to allow efficient backfolding between the sequence Pc and Pp and to avoid amplification of the backfolding part Pc, and X is an energy donor or acceptor, and a second oligonucleotide primer substantially complementary to a part of the other strand of the nucleic acid sequence to be detected;

b) after the last amplification cycle, separating the primer extension products from their complementary sequences to produce single-stranded molecules;

c) treating said single-stranded molecules containing the primer of formula I above with an oligonucleotide probe of the general formula $$Y\text{-}Pr \qquad (II)$$

wherein Y is an energy acceptor when X in the primer of formula I is an energy donor, or Y is an energy donor when X in the primer of formula I is an energy acceptor, and Pr is an oligonucleotide sequence complementary to a part of the amplified single-stranded molecules containing the primer of formula I above and selected so as to guarantee a short distance between X and Y after backfolding of the sequence Pc and hybridization of the sequence Pr to said single-stranded molecules such that an energy transfer can take place, under conditions allowing hybridization of the sequence Pc to Pp by backfolding and of Pr to the primer-I containing product; and d) determining whether an energy transfer takes place.

The present invention also relates to a primer of the general formula $$X\text{-}Pc\text{-}L\text{-}Pp \qquad (I)$$

wherein Pp is an oligonucleotide sequence substantially complementary to a part of one strand of the nucleic acid sequence to be detected, Pc is an oligonucleotide sequence substantially complementary to the sequence Pp, L is a non-nucleotidylic linker group selected so as to allow efficient backfolding between the sequence Pc and the primer Pp obtained by amplification by means of a polymerase chain reaction and to avoid amplification of the backfolding part Pc, and X is an energy donor or acceptor.

It is clear to one skilled in the art that if a sufficient amount the target nuceic acid is present in a sample, amplification may not be required. In that case, according to another embodiment of the present invention, the sample is merely treated with an oligonucleotide primer of formula (I) under hybridizing conditions such that for each different sequence to which primer I is hybridized, an extension product of said primer is created which is complementary to said nucleic acid sequence in the sample. In the context of the present invention, the "primer" extension product referred to above includes such extension products formed by polymerasion, ligation or any other known manner for incorporating said primer in the final synthesized oligonucleotide product. After incorporation of said oligonucleotide primer of formula I in an extension product, detection is then accomplished just as described above in steps b, c and d.

Furthermore, the invention relates to a diagnostic kit for amplifying and detecting at least one specific nucleic acid sequence in a sample containing a nucleic acid or a mixture of nucleic acids at least one of which is suspected of containing said sequence, which kit comprises a first container containing a primer of formula I as defined above and a second container containing a probe of formula II as defind above and means and reagents for amplification by means of a polymerase chain reaction and for detection.

The basic principles of the present invention are outlined in FIG. 1.

4. BRIEF DESCRIPTION OF THE DRAWINGS

FIG 1: Shows the steps involved in an assay for amplified DNA applying interactive labels and a backfolding primer of the general formula I and a probe of the general formula II. The complementary strand of the DNA double strand is omitted for simplification.

5. MODES FOR CARRYING OUT THE INVENTION

In the present invention, the amplification may be carried out by a combination of two primers of which at least one is a primer of the general formula I, also named "backfolding primer" due to the ability of its subsequence Pc to fold back to the primer part Pp yielding a short double strand.

It is known in the art that in oligonucleotides having selfcomplementary parts can lead to problems during hybridization by interacting with a second oligonucleotide. This is especially true if the first oligonucleotide is intended for use as a primer in a chain extension reaction using an enzyme (e.g., polymerase). To avoid these difficulties, artisans typically optimize primers, and also the probes, so as not to contain such self complementary parts.

Unexpectedly, as is further described below, applicants have discovered that oligonucleotides containing selfcomplementary regions may be quite useful in an amplification-based detection system.

In Primer (I), primer section Pp (from the 3'-end up to the nonnucleotidylic linker group L) is a standard primer typically used for the amplification of the target DNA sequence to be detected. During strand separation (e.g., such as by denaturation) and during subsequent primer extension, e.g., with a polymerase, at least part of the backfolding primer exists in the open form (i.e., see Pp in FIG. 1) and thus can specifically prime template-dependent extension in the presence of adequate amounts of the four deoxyribonucleoside triphosphates (dATP, dGTP, dTTP and dCTP) or analogs thereof.

Known DNA polymerases useful in the claimed invention include, for example, $E.$ $coli$ DNA polymerase I or its Klenow fragment, $T_4$ DNA polymerase, Taq DNA polymerase, Tth DNA polymerase from $Thermus$ $thermophilus$ and DNA polymerase from $Thermococcus$ $litoralis.$ The reaction conditions for catalyzing DNA synthesis with these DNA polymerases are known in the art.

Any amplification method which allows the incorporation of the primer I in the amplification product may be employed. By way of example, but not as a limitation, the polymerase chain reaction (PCR) is one such amplification method which is useful in the described invention. Another useful method of chain extension is the ligase chain reaction (LCR) or ligase amplification reaction (LAR). In LCR/LAR Primer (I) is directly adjacent to a second oligonucleotide (3'- and 5' ends are adjacent) when hybridized to a complementary DNA template. Amplification occurs through repeated denaturation, primer annealing and ligation of the 3'- and 5'-ends of the oligonucleotides. LCR/LAR has been described by Wu and Wallace in Genomics 4, 560–569 (1988). The amplification products containing the labeled primer of formula I may then be detected by hybridizing a labeled probe of formula II near to the backfolded piece Pc as described in the next paragraphs.

In the present invention, if amplification is performed, PCR is the contemplated preferred method.

Strand separation by temperature denaturation takes place at about 90°–100° C. Primer extension using a polymerase usually occurs at a lower temperature depending in part on the polymerase used. When Taq polymerase is used, the primer extension temperature is usually between 70°–80° C. This temperature is just high enough to prevent complete internal backfolding of the short sequence Pc to Pp in primer (I), which otherwise might inhibit the primer activity.

After amplification, the temperature is typically lowered allowing the incorporated primer, especially its part Pc, to fold back upon itself ("backfolding") as shown in FIG. 1. A probe of formula (II) (detection oligonucleotide) having at its 3'-end one or more energy donor molecules (if X in primer (I) is an energy acceptor) or an energy acceptor molecule (if X in the primer (I) is an energy donor molecule) is then hybridized to the amplified region downstream of the backfolding segment Pc of Primer (I). The backfolding thus guarantees a short distance between the donor or the acceptor at the 5'-end of the backfolding primer thereby permitting energy to be transferred as shown in FIG. 1, step b). In the context of this invention the "short" distance between X and Y referred to above means a distance which ensures efficient energy transfer, the measurement of which is easily determined by one skilled in the art. Presently, such distance is contemplated to be no more than about 10 nucleotides. If the target sequence is not present and therefore has not been amplified by primer (I), this energy transfer will not take place inasmuch as there is no primer extension product to which the detection oligomer can hybridize. Therefore a clearcut distinction between the presence of the amplified target or its absence is possible. Thus, detection can be carried out directly after amplification in a homogeneous format without having to perform separation steps. In such a format, an energy transfer indicates the presence of the amplified target sequence.

Primer (I) may be of any length suitable for amplification and detection. Primer section Pp preferably has a length of about 10 to about 30 nucleotides, but may be shorter or longer, depending on the sequence to be detected. Parameters for designing sequence and temperature specific PCR primers are known in the art. For example, it is known to take into account the stability of the individual base pairings of the nucleotide bases. See, e.g., Bukh, Purcell, and Miller "Importance of primer selection for the detection of hepatitus C virus RNA with the polymerase chain reaction assay," *Proc Natl Acad Sci* USA. [89]: p. 187–191 (1991); Lowe, et al., "A computer program for selection of oligonucleotides primers for polymerase chain reaction," *Nucl Acids Res.* [18]: p. 1757–1761 (1990); Rozas, "A program to optimize the design of oligonucleotides for PCR amplification," *J. Heredity.* [82]: p. 84 (1991); Wu, et al. "The effect of temperature and oligonucleotide primer length on the specificity and efficiency of amplification by the polymerase chain reaction," *DNA and Cell Biol.* [10]: p. 233–238 (1991); *PCR Protocols,* White et al. editor (Academic Press, Inc. 1990), pp. 15–16.

Primer section Pp is selected to be "substantially" complementary to each specific sequence to be amplified. Primer section Pp need not reflect the exact sequence of the template, but must be sufficiently complementary to selectively hybridize to the template even at the temperature of polymerisation. Non complementary bases or longer sequences can be interspersed into the primer section Pp provided that this section retains sufficient complementarity with the sequence of one of the strands to be amplified to hybridize therewith, and to thereby form a duplex structure which can be extended by the extension, e.g., polymerizing, agent. Preferably, primer section Pp is complementary to the sequence of the template.

Primer section Pc will be adapted in each case to be partially or completely complementary to the sequence of section Pp.

Applicants have unexpectedly found that addition of backfolding part Pc, together with the label, is not detrimental to the primer's function. The sequence of Pc may have any length relative to Pp. Preferably, Pc is shorter than Pp by a few bases. Otherwise, if Pc were longer than Pp, then it is possible that it might bind more tightly than Pp to the complementary sequence of the template at the amplification temperature, thereby interfering with the intended reaction. Additional donor molecules can span the gap the between 3'-end of probe (II) and 5'-end of primer (I). It is not required that the 3'-end of the probe (II) start exactly where the 5'-end of the backfolded prime (I) ends.

Additionally, primer section Pp should not be too long in relation to Pc so as to avoid having the probe hybridize to the backfolded primer (I) prior to primer extension (elongation) which might result particularly at lower temperatures and yield false positive results. The length of each of the subsections of primer (I) also depends on the composition of the bases in each of these sections.

The second oligonucleotide primer (sometimes called the "counter primer") commonly used for coamplification of the other (complementary) nucleic add strand may also be labeled and used in equal or different amounts than primer (I). If both primers are labeled, almost all amplified sequences will be labeled and can be detected using at least one 3'-labeled probe (II) which allows hybridization near to the backfolded part Pc of at least one of the nucleic acid sequences to be detected after amplification. Other variations or combinations of the primers of the invention and the probes described are within the scope of the present invention such as, for example, the use of differently labeled primers, single strand amplification or RNA amplification instead of DNA.

Alternatively, one can also place one or more of the donor molecules at the 5'-end of the backfolding section of Primer (I) and the acceptor molecules at the 3'-end of the probe as is shown schematically in FIG. 1, step c). Preferably, the primer will be labeled with the energy donor at the 5'-end. This may be advantageous due to the background fluorescence of the energy acceptor resulting from direct excitation. In PCR, the primers are applied in large excess. Thus, if the primer is labeled with the energy acceptor (e.g. the Ru complex), this fluorescence caused by direct excitation may become important.

The detection of the energy transfer between the donor and the acceptor by fluoresence measurements is performed by methods known in the art. The methodology of the time-resolved fluorescence technique is described, for example, in the German Offenlegungsschrift No. 2628158 and in the European Patent Application, Publ. No. 178 450.

Interactive molecule complexes may be used in any combination in the present invention, provided that they are chemically bonded or complexed to the primer or the probe without affecting the optical properties of these molecules and that they are clearly detectable in the presence of DNA. Suitable interactive molecules for use in the present invention are glucose oxidase/peroxidase; fluorescein/rhodamin, salicylate/terbium and acridinium/rhodamine complexes. The donor/acceptor combination lumazine chromophore/bathophenan-throline-ruthenium-II-complex is preferred.

In the present invention, the backfolding primer I also includes a nonnucleotidylic group L which allows a base pairing of the complementary bases in Pc and Pp, thereby avoiding loop formation. This nonnucleotidylic group leads also to a stop of the polymerase at this position during the amplification process.

The nonnucleotidylic group L is selected so as to allow efficient backfolding between the sequence Pp and its complementary sequence Pc. This group L may consist of any kind of nonnucleotidylic linkers which allow defined backfolding of Pc to Pp without loop formation. Preferably, the nonnucleotidylic linker is derived from propanediol. More preferably, the linker group L consists of two propanediol units linked together by a phosphate group and attached via phosphate groups to the oligonucleotide sequences Pc and Pp. The most preferred linker group L has the following formula:

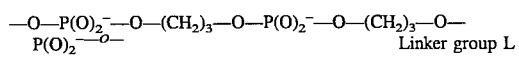

Linker group L

This nonnucleotidylic linker has been found unexpectedly to allow efficient backfolding of Pc to Pp and additionally to avoid amplification of the backfolding part Pc.

The following description serves to illustrate some of the steps involved in the preparation of the labeled primers and probes and performing the process of the present invention.

The oligonucleotides which act as normal primers in the polymerase reaction or the oligonucleotides which are parts of the modified primers or probes can be synthesized by methods known in the art. Reference is made, for example, to M. J. Gait (Ed.), DNA-Synthesis—A Practical Approach, IRL-Press, 1984. Solid phase synthesis using β-cyanoethyl phosphoramidites as described by N. D. Sinha et al., in Nucleic Acids Research 12, 4539–4557 (1984), is preferred.

The group L may be inserted in the course of the solid phase synthesis of the primer part Pp with phosphoramidite 5 (below) or analogs thereof. The synthesis of complex 5 below is described by F. Seela in Nucleic Acids Research 15, 3113 (1987).

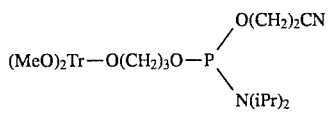

5

Adding two of these amidites 5 to the oligonucleotide Pp during the synthesis yields the most preferred linker which will be further elongated during the synthesis with the appropriate nucleoside phosphoramidites to add the backfolding part Pc of the primer of formula I.

The energy transfer labels of the present invention which are selected for coupling at the 3'- or 5'-OH group at the end of the primer or probe may be coupled either directly to the primers or probes or after modifying these terminal hydroxy groups into —NH$_2$, —COOH, —SH or any other suitable terminal group using methods known in the art. The attachment of the labels may be done both if the oligonucleotide is still bonded to the support or if it is already cleaved off. The labels may also be introduced in one or more of the nucleotide bases of the primers or probes prior to their attachment to the growing oligonucleotide chain in form of, for example, nucleoside amidites. In case of Ru complex/ lumazine labels, the lumazine group may be introduced at the 5'-end of the backfolding primer or at the 3'-end of the probe using phosphoramidite 7 (below), of 6,7-dimethyl lumazine-2'-deoxyriboside. Other lumazine derivatives or coupling reagents for the introduction of the phosphate group may also be used.

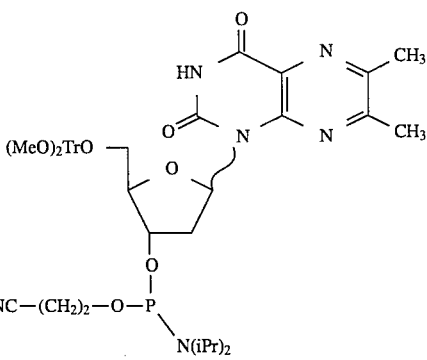

One or more of these molecules bearing the lumazine chromophore may be introduced in the oligonucleotide to enhance the energy transfer. Preferably, one to four consecutive lumazine chromophores are incorporated. The synthesis and introduction of the lumazine ribosides either at the 3'- or 5'-end of an oligonucleotide is described in the European Patent Application, Publ. No. 439 036.

The use of Ru complexes having various different spacers between the Ru complex and the DNA molecule to which it is attached, as energy acceptors has been described in European Patent Application Publ. Nos. 340 605 and 178 450. For the attachment of the Ru complex at the 5'-end of the backfolding section of the primer, a phosphoramidite structure 6a (below) or a reagent of structure 6b (below) may be used. Preferably, the derivative 6b is used for the introduction of the Ru complex at the 3'-end.

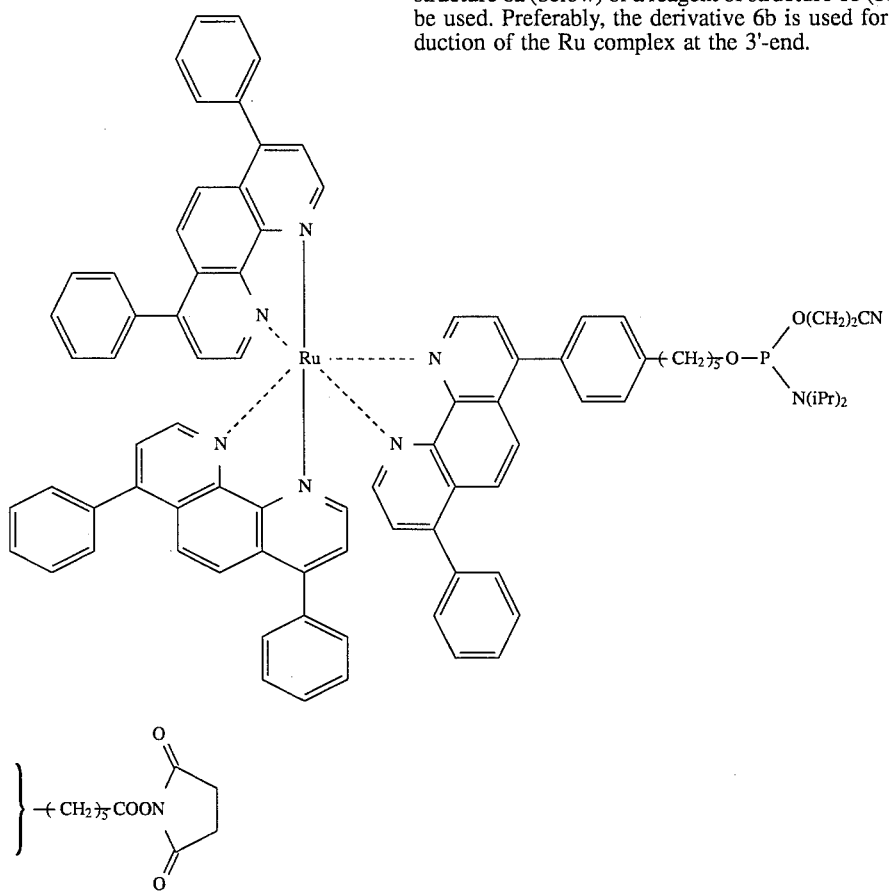

The reagent 6a can be used without further modifications for coupling, inter alia, to a hydroxy or amino group in the course of the solid phase synthesis of the oligonucleotide.

Coupling of reagent 6b at the 3'-end may be performed after some modifications of the solid support used for the synthesis. The general scheme (Scheme 1) for such coupling when starting with compound 8 has been described by Nelson et al. in Nucleic Acids Research 17, 7179 (1989) as is shown below. For further details, including the attachment of the Ru complex derivative 6b to the modified support 10, see Example 2 infra.

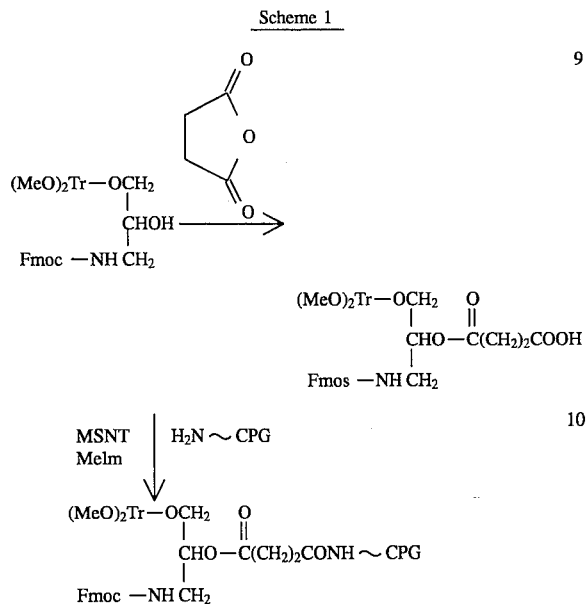

Scheme 1

EXAMPLES

The invention is further illustrated by the following examples, which are presented merely by way of illustrating the invention and are not limitations to said invention.

Example 1

Synthesis of Lumazine and Ru complex phosphoramidites
The phosphoramidite of 6,7-dimethyl-lumazine-2'-deoxyriboside was prepared as described in European Patent Application Publication No. 439 036 (Jul. 31, 1991). The phosphoramidite 6a of the Ru complex was prepared in situ as described by W. Bannwarth and D. Schmidt in Tetrahedron Letters 30, 1513–1516 (1989).

Ru complex derivative 6b was prepared by coupling the Ru complex with activated N-hydroxysuccinimide as described in European Patent Application Publ. No. 340 605 also appearing in (W. Bannwarth et al., in Helvetica Chimica Acta 71 2085–2099 (1988)). N,N,N',N'-tetramethyl (succinimido) uronium tetrafluoroborate (TSTU) was used as an activating agent. The synthesis and use of TSTU is described in R. Knorr et al., Tetrahedron Letters 30, 1927–1930 (1989) and in W. Bannwarth in Tetrahedron Letters 32, 1157–1160 (1991).

Synthesis of 1-O-(4,4'-dimethoxytrityl)-3-O-((N,N-diisopropylamino)-β-cyanoethoxy-phosphino)-1,3-propanediol 5

This reagent was prepared in a two step procedure as described by F. Seela and K. Kaiser in Nucleic Acids Research 15, 3113–3129 (1987) starting from 1,3-propanediol which was first protected by a 4,4'-dimethoxytrityl group. This was followed by a phosphinylation with (β-cyanoethoxy) bis (diisopropylamino) phosphine in the presence of diisopropylammonium tetrazolide to yield compound 5.

Example 2

Synthesis of 3'-Ru complex modified DNA
The synthesis of the modified controlled pore glass (CPC) support for the solid phase synthesis of 3'-modified oligonucleotides was done as outlined in Scheme 1 (above).

Compound 8 was prepared according to the procedure described by Nelson et al., in Nucleic Acids Research 17, 7179–7186 and 7187–7194 (1989).

In the next step, compound 8 (10 mmol; 6.16 g) was evaporated three times from anh. pyridine. Then it was dissolved in 60 ml of anh. pyridine and 25 mmol (2.50 g) of succinic acid anhydride and 10 mmol (1.22 g) of 4-dimethylaminopyridin (DMAP) were added and stirred under argon. After 4 hours, the reaction was finished as noted by TLC. The reaction mixture was taken up in 200 ml of diethylether and extracted four times with saturated brine. The organic layer was dried over $Na_2SO_4$ and evaporated, yielding 6 g of an oil. The oil was then purified by short column chromatography (CC) on 50 g of silica gel (0,003–0, 040 nm (Merck)) with 1000 ml of a mixture of $CH_2Cl_2$/MeOH/pyridine (94:5:1; v/v), 500 ml of $CH_2Cl_2$/MeOH/pyridine (92:7:1) and 500 ml of $CH_2Cl_2$/MeOH/pyridine (89:10:1). Pure fractions were collected and precipitated from n-pentane yielding 2.3 g of pure Compound 9. M.p. 87°–89° C.

Anal. calculated for $C_{43}H_{41}NO_9$.0.2 n-pentane: C 72.37, H 5.99, N 1.92; found: C 72.60, H 6.14, N 1.94. $^1$H-NMR ($CDCl_3$): 2.64 (s, $OCCH_2CH_2CO$); 3.03–3.50 (2m, $CH_2$—CH—$CH_2$); 3.50–3.65 (m, $CH_2$—CH—$CH_2$); 3.74 (s, 2 $OCH_3$); 4.19 (t, $CH_2$—CH); 4.34 (d, $CH_2$—CH); 6.81 (d, 4 arom. H, $C_6H_4$); 7.15–7.37 (m, 9 arom. H, $C_6H_5,C_6H_4$); 7.39 (t, fluorenyl); 7.51 (d, fluorenyl); 7.76 (d, fluorenyl).

Functionalized support 10 was prepared as follows.
The CPG-support (Pierce) was evaporated from anh. pyridine. Then it was dissolved in 10 ml of anh. pyridine and 0.60 mmol (430 mg) of 9 as well as 3 mmol (880 mg) of 1-(mesitylen-2-sulfonyl)-3-nitro-1H-1,2,4-triazole (MSNT) and 0.3 ml of N-methyl imidazole (NMI) were added, and the suspension was allowed to react at room temperature with occasional shaking. After 2 hours, it was filtered off and washed successively with pyridine, DMF and ether. To the support 10 ml were added of a mixture of $Ac_2O$ pyridine (1/10; v/v) containing 1% DMAP. After 1 h it was filtered off and the support washed with pyridine, DMF, ethanol and ether. The degree of functionalization of support 10 was determined by photometric determination of the dimethoxytrityl cation (30.5 mmol/g) measured at 498 nm. Functionalization was also measured by cleavage of the fluorenylmethoxycarbonyl (Fmoc) group, the measurement of which was taken at 300 nm (30.1 mmol/g).

Preparation of the 3'-amino modified DNA on support 10.
The synthesis was carried out on a synthesizer starting with 1.5 mmol of support 10. A tenfold excess of the corresponding phosphoramidites was applied during each cycle. After synthesis the support was washed with acetonitril and ether, and dried. Then 20 mg of the support were treated with 700 μl of conc. ammonia for 1.5 h at 67° C. in a tightly dosed Eppendorf tube. The suspension was filtered and the filtrate taken to dryness. The pellet obtained was dissolved in 300 μl of 80% acetic add and after 2 h, 700 μl of ether were added to precipitate the DNA. After centrifuging, the pellet was dissolved in water and after addition of 500 mmol of KCl it was dialysed against 2 liters of water (excl. MW 1000). UV absorbancy indicated a yield of 53 optical density (OD) (measured at 260 nm) units of amino modified DNA, which was used as such for the coupling to the Ru complex.

Coupling of 6b to the amino modified DNA.

In an Eppendorf tube 27.5 OD units of the 3'-amino modified DNA and 4 mmol (3 mg) of 6b were reacted in a mixture of 200 µl of DMF, 200 µl of dioxane, 200 µl of water and 5 µl of Hünigs base. The mixture was allowed to react for 16 hours with shaking in the dark. It was taken to dryness in a speed vac concentrator and dissolved in 500 µl of water. The solution was extracted 3 times with 500 µl of $CHCl_3$ to remove the excess of Ru complex. The purification was performed by polyacrylamide gel electrophoresis followed by electroelution.

Example 3

Synthesis of the oligonucleotides with a nonnucleotidylic linker and/or 3' or 5' modifications.

Oligonucleotides without modifications were prepared on controlled pore glass (CPG, Pierce) and applying β-cyanoethyl phosphoramidites of the appropriate building blocks. 3'-Lumazine modified oligonucleotides were prepared by elongation of lumazine-2'-deoxyriboside modified CPG-support as described in European Patent Application Publ. No. 439 036. This application also describes methods and reagents for use in the synthesis of 5'-lumazine and 5'-Ru complex-modified oligonucleotides.

The nonnucleotidyl linker group consisting of two propanediol units separated by a phosphate group was inserted in the course of the solid phase synthesis with the corresponding phosphoramidite 5. Coupling of this amidite was performed twice, using a 10 fold excess and about 3 minutes coupling time together with tetrazole as activating agent.

The addition of the Ru complex at the 3'-end of the oligonucleotide was performed with Ru complex derivative 6b after the synthesis and deprotection of the oligonucleotide as described in Example 2.

Example 4

Polymerase chain reaction with a primer of the general formula I.

Several oligonucleotides were synthesized and tested for their ability to act as primers in the polymerase chain reaction. The DNA fragment selected for amplification is part of the gag region of HIV-1. Conventional primers with (16) or without (14,15) an Ru complex at the 5'-end as well as modified primers of the general formula I (17,18) were synthesized with methods already described.

The primers had the following specific sequences:
5'A-T-A-A-T-C-C-A-C-C-T-A-T-C-C-C-A-G-T-A-G-G-A-G-A-A-A-T₃.14
(SEQ ID NO:1)
5'T-A-T-C-C-A-G-T-A-G-G-A-G-A-A-A-T₃.15
(SEQ ID NO:2)
5'Ru-T-A-T-C-C-G-A-G-T-A-G-G-A-G-A-A-A-T₃.16
(Ru-SEQ ID NO:3)

In each case the second primer or counter primer used for coamplification of the complementary strand had the following sequence:
5'T-T-T-G-G-T-C-C-T-T-G-T-C-T-T-A-T-G-T-C-C-A-G-A-A-T-G-C₃.19
(SEQ ID NO:8)

These oligonucleotides were derived from primer and probe sequences already described in Table 2 of C. H. Ou et al., in Science 239, 295–297 (1988).

In each amplification reaction 1000 copies of HIV plasmid DNA were applied. The primers were used in excess at 100 pMoles. In case of primer 19, 50 pMoles were used. The HIV DNA was amplified in duplicate and a PCR negative control was incorporated. Amplification with primers 14 and 19 was used as positive controls.

50 µl of HIV DNA were added to 50 µl master mix for a total volume of 100 µl per reaction mixture.

| Master mix: | | |
|---|---|---|
| | Distilled water | 27.5 µl |
| | 10×Taq buffer | 10.0 µl |
| | 8 mM dNTP | 10.0 µl |
| | 100 mM primer (14–18) | 3.0 µl |
| | 50 mM primer 19 | 3.0 µl |
| | Taq polymerase | 0.5 µl |

The efficiency and the homogeneity of the amplified DNA was tested by Southern hybridization (E. M. Southern, Journal of Molecular Biology 98, 503 (1975), using the radio labeled probe 5' ATC CTG GGA TTA A3' (SEQ ID NO:9). The hybridizations were all carried out in a phosphate-buffered saline solution (10 mM inorganic phosphate; 1M NaCl, pH 7.0) with the oligonucleotides in equimolar ratio. Even the shortest backfolding primer equipped at the 5'-end with a Ru complex leads to a specific amplification comparable in efficiency with a standard nonmodified primer.

Example 5

Detection of elongated backfolding primers via hybridization and energy transfer It was determined whether a backfolding primer of the general formula I after its elongation in a polymerase chain reaction is able to serve as a template for subsequent detection with an oligonucleotide probe of the general formula II. 5'-Ru-complex-labeled oligonucleotide 1 serves as a synthetic model compound for an elongated primer of structure I which acts as a template for 3-lumazine-labeled probes 2a, 2b and 2d and negative probe 2c.

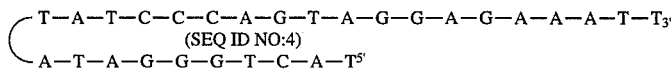

17

(SEQ ID NO:5)

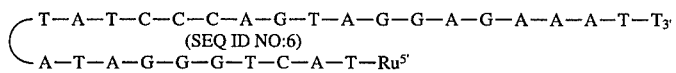

18

(SEQ ID NO:7-Ru)

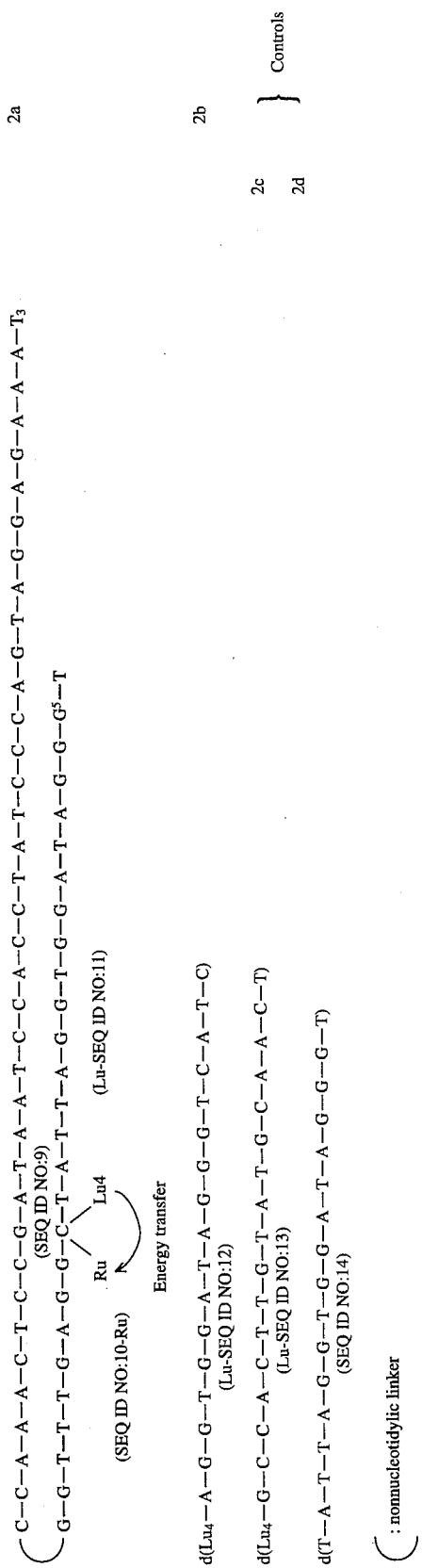

Hybridizations were all carried out in a phosphate-buffered saline solution (10 mM inorganic phosphate; 1M NaCl, pH 7.0) with oligonucleotides in equimolar ratio.

Fluorescence measurements were performed on a SLM Model 4048 S spectrofluorometer. Excitation and emission wavelengths were set at 337 nm and 620 nm, respectively. The concentrations of the hybrids were $1.3 \cdot 10^{-6}$ M for a sample volume of 400 µl.

Table 1 shows the results of the energy transfer measurements. As expected, the results were positive in case of probes 2a and 2b and negative in case of probes 2c and 2d.

TABLE 1

| Hybrid | $IF/IF_2$ |
|--------|-----------|
| 1/2a   | 2.1       |
| 1/2b   | 2.1       |
| 1/2c   | 1.0       |
| 1/2d   | 1.2       |

The fluorescence resulting from the energy transfer ($IF_3$) was defined as being the difference between the measured fluorescence at 620 nm (IF) minus the fluorescence of the Ru complex through direct excitation ($IF_2$) and the fluorescence of the lumazine chromophore at 620 nm ($IF_1$), which can be neglected. Therefore the formula for the intensity of the energy transfer reduces to: $IF_3 = IF - IF_2$. For the sake of simplicity we have shown in Table 1 only the ratio of the measured fluorescence intensity IF at 620 nm in relation to the fluorescence intensity of the Ru complex due to direct excitation ($IF_2$).

The reversed energy transfer system utilizing a 5'-lumazine-labeled primer and a 3'-Ru complex-labeled probe was investigated with model compounds 11, 12 and 13.

T–A–T–C–C–C–A–G–T–A–G–G–A–G–A–A–T–T–A–A–A–G–A–T–G–A–T–A–A₃'
(SEQ ID NO:15)
A–T–A–G–G–G–T–C–A–T–Lu₆    Ru–T–A–A–A–T–A–T–T–T–C–T–A–C–C–T–A–T–T⁵'
(SEQ ID NO:16-Lu)            (Ru-SEQ ID NO:17)

energy transfer

T–A–T–C–C–C–A–G–T–A–G–G–A–G–A–A–T–T–A–A–A–A–G–A–T–G–A–T–A–A₃'
(SEQ ID NO:18)
A–T–A–G–G–T–C–A–T–C–C–T–C–T–T          Ru–T–A–A–A–T–A–T–T–T–C–T–A–C–C–T–A–T–T⁵'
(SEQ ID NO:19)                                                    (Ru-SEQ ID NO:20)

no energy transfer

The results obtained with the primer/probe systems 11/12 (showing energy transfer) and 13/12 as a negative control with no energy transfer confirmed the utility of this combination, although the efficiency for the energy transfer was a bit lower (data not shown).

We claim:

1. A process for detecting the presence or absence of at least one specific nucleic acid sequence in a sample suspected of containing said sequence, which process comprises:

a) amplifying the nucleic acid sequence to be detected by means of a chain extension reaction utilizing a first oligonucleotide primer of general formula 5'-X-Pc-L-Pp-3'    (I)

wherein Pp is an oligonucleotide sequence substantially complementary to a part of one strand of the nucleic acid sequence to be detected, Pc is an oligonucleotide sequence substantially complementary to and not longer than the sequence Pp, L is a non-nucleotidylic linker group selected so as to allow efficient backfolding between sequences Pc and Pp, and X is an energy donor or acceptor, and a second oligonucleotide primer substantially complementary to a part of the other strand of the nucleic acid sequence to be detected, and wherein primer extension occurs at a temperature which is high enough to prevent complete internal backfolding of Pc to Pp, utilizing a thermostable enzyme;

b) separating after a last amplification cycle the primer extension products of step (a) from their complementary sequences to produce single-stranded molecules containing a primer of formula I;

c) treating said single-stranded molecules containing a primer of formula I with an oligonucleotide probe of the general formula

3'-Y-Pr-5'    (II)

wherein Y is an energy acceptor when X in the primer of formula I is an energy donor, or is an energy donor when X in the primer of formula I is an energy acceptor, and Pr is an oligonucleotide sequence complementary to a part of the amplified single-stranded molecules containing the primer of formula I above and selected so as to guarantee a distance between X and Y that allows for energy transfer between X and Y after backfolding of the sequence Pc and hybridization of the sequence Pr to said single-stranded molecules such that an energy transfer can take place, under conditions allowing hybridization of the sequences Pc to Pp by backfolding and of Pr to said single-stranded molecules containing a primer of formula I; and d) determining whether an energy transfer takes place as a means for detecting the presence or absence of the nucleic acid sequence to be detected.

2. The process of claim 1, wherein X is an energy donor and Y is an energy acceptor.

3. The process of claim 1, wherein X is an energy acceptor and Y is an energy donor.

4. The process of claim 1, wherein the energy donor is a lumazine chromophore.

5. The process of claim 1, wherein the energy acceptor is a bathophenanthroline-ruthenium-II-complex.

6. The process of claim 1, wherein L consists of two propanediol units linked together by a phosphate group and attached via phosphate groups to the oligonucleotide sequences Pc and Pp.

7. The process of claim 1, wherein amplification is accomplished by the polymerase chain reaction.

8. A primer of the general formula

5'-X-Pc-L-Pp-3'    (I)

wherein Pp is an oligonucleotide sequence substantially complementary to a part of one strand of the nucleic acid sequence to be detected, Pc is an oligonucleotide sequence substantially complementary to and not longer than the sequence Pp, L is a non-nucleotidylic linker group, consisting of two propanediol units linked together by a phosphate group and attached via phosphate groups to the oligonucleotide sequences Pc and Pp provided that during the formation of said primer extension sequence during said amplification, oligonucleotide Pc is not completely internally backfolded, and X is an energy donor or acceptor.

9. The primer of claim 8, wherein X is an energy donor.

10. The primer of claim 8, wherein X is an energy acceptor.

11. The primer of claim 8, wherein X is a lumazine chromophore.

12. The primer of claim 8, wherein X is a bathophenanthroline-ruthenium-II-complex.

13. A kit for amplifying at least one specific nucleic acid sequence in a sample containing a nucleic add or a mixture of nucleic acids at least one of which is suspected of containing said sequence, which kit comprises a primer of formula I as defined in claim 8.

14. The kit of claim 13 which also includes a detection probe.

15. A non-nucleotidylic linker group having the formula

—O—P(O)$_2^-$—O—(CH$_2$)$_3$—O—P(O)$_2^-$—O—(CH$_2$)$_3$—O—P(O)$_2^-$—O—.

16. A process for detecting the presence or absence of at least one specific nucleic acid sequence in a sample suspected of containing said sequence, which process comprises:

a) treating the sample with a first oligonucleotide primer of general formula

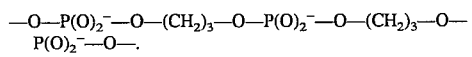

5'-X-Pc-L-Pp-3' wherein Pp is an oligonucleotide sequence substantially complementary to a part of one strand of the nucleic acid sequence to be detected, Pc is an oligonucleotide sequence substantially complementary to and not longer than the sequence Pp, L is a non-nucleotidylic linker group selected so as to allow efficient backfolding between sequences Pc and Pp, and X is an energy donor or acceptor, under hybridizing conditions such that for each different nucleic acid sequence to which primer I is hybridized, an extension product of said primer is created which is complementary to said nucleic acid sequence, and wherein primer extension occurs at a temperature which is high enough to prevent complete backfolding of Pc to Pp, utilizing a thermostable enzyme;

b) separating said extension products of said primer I from their complementary sequences to produce single-stranded molecules;

c) treating said single-stranded molecules with an oligonucleotide probe of the general formula

3'-Y-Pr-5'    (II)

wherein Y is an energy acceptor when X in the primer of formula I is an energy donor, or an energy donor when X in the primer of formula I is an energy acceptor, and Pr is an oligonucleotide sequence complementary to a part of the amplified single-stranded molecules containing the primer of formula I above and selected so as to guarantee a distance between X and Y that allows for energy transfer between X and Y after backfolding of the sequence Pc and hybridization of the sequence Pr to said single-stranded molecules such that an energy transfer can take place, under conditions allowing hybridization of the sequences Pc to Pp by backfolding and of Pr to the extension product of Primer I; and d) determining whether energy transfer occurs as a means for detecting the presence or absence of the nucleic acid sequence to be detected.

17. A process for detecting the presence or absence of at least one specific nucleic acid sequence in a sample suspected of containing said sequence, which process comprises:

a) amplifying the nucleic acid sequence to be detected by means of a chain extension reaction utilizing a first oligonucleotide primer of general formula 5'-X-Pc-L-Pp-3'     (I)

wherein Pp is an oligonucleotide sequence substantially complementary to a part of one strand of the nucleic acid sequence to be detected, Pc is an oligonucleotide sequence substantially complementary to and not longer than the sequence Pp, L is a non-nucleotidylic linker group selected so as to allow efficient backfolding between sequences Pc and Pp, and X is an energy donor or acceptor, and a second oligonucleotide primer substantially complementary to a part of the other strand of the nucleic acid sequence to be detected, and wherein primer extension occurs at a temperature of at least about 70° C., using a thermostable enzyme;

b) separating after a last amplification cycle the primer extension products of step (a) from their complementary sequences to produce single-stranded molecules containing a primer of formula I;

c) treating said single-stranded molecules containing a primer of formula I with an oligonucleotide probe of the general formula 3'-Y-Pr-5'     (II)

wherein Y is an energy acceptor when X in the primer of formula I is an energy donor, or is an energy donor when X in the primer of formula I is an energy acceptor, and Pr is an oligonucleotide sequence complementary to a part of the amplified single-stranded molecules containing the primer of formula I above and selected so as to guarantee a distance between X and Y that allows for energy transfer between X and Y after backfolding of the sequence Pc and hybridization of the sequence Pr to said single-stranded molecules such that an energy transfer can take place, under conditions allowing hybridization of the sequences Pc to Pp by backfolding and of Pr to said single-stranded molecules containing a primer of formula I; and d) determining whether an energy transfer takes place as a means for detecting the presence or absence of the nucleic acid sequence to be detected.

18. A process for detecting the presence or absence of at least one specific nucleic acid sequence in a sample suspected of containing said sequence, which process comprises:

a) treating the sample with a first oligonucleotide primer of general formula

5'-X-Pc-L-Pp-3'     (I)

wherein Pp is an oligonucleotide sequence substantially complementary to a part of one strand of the nucleic acid sequence to be detected, Pc is an oligonucleotide sequence substantially complementary to and not longer than the sequence Pp, L is a non-nucleotidylic linker group selected so as to allow efficient backfolding between sequences Pc and Pp, and X is an energy donor or acceptor, under hybridizing conditions such that for each different nucleic acid sequence to which primer I is hybridized, an extension product of said primer is created which is complementary to said nucleic acid sequence, and wherein the temperature at which primer extension occurs is at least about 70° C., using a thermostable enzyme;

b) separating said extension products of said primer I from their complementary sequences to produce single-stranded molecules;

c) treating said single-stranded molecules with an oligonucleotide probe of the general formula 3'-Y-Pr-5'     (II)

wherein Y is an energy acceptor when X in the primer of formula I is an energy donor, or an energy donor when X in the primer of formula I is an energy acceptor, and Pr is an oligonucleotide sequence complementary to a part of the amplified single-stranded molecules containing the primer of formula I above and selected so as to guarantee a distance between X and Y that allows for energy transfer between X and Y after backfolding of the sequence Pc and hybridization of the sequence Pr to said single-stranded molecules such that an energy transfer can take place, under conditions allowing hybridization of the sequences Pc to Pp by backfolding and of Pr to the extension product of Primer I; and d) determining whether energy transfer occurs as a means for detecting the presence or absence of the nucleic acid sequence to be detected.

19. A process for detecting the presence or absence of at least one specific nucleic acid sequence in a sample suspected of containing said sequence, which process comprises:

a) amplifying the nucleic acid sequence to be detected by means of a chain extension reaction utilizing a first oligonucleotide primer of general formula 5'-X-Pc-L-Pp-3'     (I)

wherein Pp is an oligonucleotide sequence substantially complementary to a part of one strand of the nucleic acid sequence to be detected, Pc is an oligonucleotide sequence substantially complementary to and not longer than the sequence Pp, L is a non-nucleotidylic linker group selected so as to allow efficient backfolding between sequences Pc and Pp, and X is an energy donor or acceptor, and a second oligonucleotide primer substantially complementary to a part of the other strand of the nucleic acid sequence to be detected;

b) separating after a last amplification cycle the primer extension products of step (a) from their complementary sequences to produce single-stranded molecules containing a primer of formula I;

c) treating said single-stranded molecules containing a primer of formula I with an oligonucleotide probe of the general formula 3'-Y-Pr-5'     (II)

wherein Y is an energy acceptor when X in the primer of formula I is an energy donor, or is an energy donor when X in the primer of formula I is an energy acceptor, and Pr is an oligonucleotide sequence complementary to a part of the amplified single-stranded molecules containing the primer of formula I above and selected so as to guarantee a distance between X and Y that allows for energy transfer between X and Y after backfolding of the sequence Pc and hybridization of the sequence Pr to said single-stranded molecules such that an energy transfer can take place, under conditions allowing hybridization of the sequences Pc to Pp by backfolding and of Pr to said single-stranded molecules containing a primer of formula I; and d) determining whether an energy transfer takes place as a means for detecting the presence or absence of the nucleic acid sequence to be detected.

20. A process for detecting the presence or absence of at least one specific nucleic acid sequence in a sample suspected of containing said sequence, which process comprises:

a) treating the sample with a first oligonucleotide primer of general formula

wherein Pp is an oligonucleotide sequence substantially complementary to a part of one strand of the nucleic acid sequence to be detected, Pc is an oligonucleotide sequence substantially complementary to and not longer than the sequence Pp, L is a non-nucleotidylic linker group selected so as to allow efficient backfolding between sequences Pc and Pp, and X is an energy donor or acceptor, under hybridizing conditions such that for each different nucleic acid sequence to which primer I is hybridized, an extension product of said primer is created which is complementary to said nucleic acid sequence;

b) separating said extension products of said primer I from their complementary sequences to produce single-stranded molecules;

c) treating said single-stranded molecules with an oligonucleotide probe of the general formula

                           (II)

wherein Y is an energy acceptor when X in the primer of formula I is an energy donor, or an energy donor when X in the primer of formula I is an energy acceptor, and Pr is an oligonucleotide sequence complementary to a part of the amplified single-stranded molecules containing the primer of formula I above and selected so as to guarantee a distance between X and Y that allows for energy transfer between X and Y after backfolding of the sequence Pc and hybridization of the sequence Pr to said single-stranded molecules such that an energy transfer can take place, under conditions allowing hybridization of the sequences Pc to Pp by backfolding and of Pr to the extension product of Primer I; and d) determining whether energy transfer occurs as a means for detecting the presence or absence of the nucleic acid sequence to be detected.

21. The process of claim 1 wherein the thermostable enzyme is Taq polymerase.

* * * * *

UNITED STATES PATENT AND TRADEMARK OFFICE
CERTIFICATE OF CORRECTION

PATENT NO. : 5,573,906
DATED : November 12, 1996
INVENTOR(S) : Wilhelm Bannwarth, Francis Muller It is certified that error appears in the above-indentified patent and that said Letters Patent is hereby corrected as shown below:

In claim 13, column 30, line 13 please replace "add" with -- acid --.

Signed and Sealed this

Twenty-sixth Day of August, 1997

Attest:

BRUCE LEHMAN

Attesting Officer

Commissioner of Patents and Trademarks